United States Patent
Chiu et al.

(10) Patent No.: US 6,441,067 B1
(45) Date of Patent: Aug. 27, 2002

(54) PHOSPHORUS-CONTAINING COMPOUNDS AND THEIR USE IN FLAME RETARDANCE

(75) Inventors: Yie-Shun Chiu; Meng-Dan Jiang, both of Tao-Yuan; Ying-Ling Liu, Chung-Li, all of (TW)

(73) Assignee: Chung-Shan Institute of Science & Technology, Tao-Yuan (TW)

( * ) Notice: Subject to any disclaimer, the term of this patent is extended or adjusted under 35 U.S.C. 154(b) by 0 days.

(21) Appl. No.: 09/934,705

(22) Filed: Aug. 23, 2001

(51) Int. Cl.$^7$ .............................. C08K 5/49; C07C 69/76
(52) U.S. Cl. ............................ 524/117; 558/76; 558/82
(58) Field of Search ...................... 558/76, 82; 524/117

(56) References Cited

U.S. PATENT DOCUMENTS 3,702,878 A * 11/1972 Saito et al. .................. 524/117
4,198,492 A * 4/1980 Izawa et al. ................. 525/134

* cited by examiner

Primary Examiner—Kriellion Sanders
(74) Attorney, Agent, or Firm—Bacon & Thomas

(57) ABSTRACT

A series of novel phosphorus-containing compounds suitable for use as a flame retardant having the following formula are disclosed:

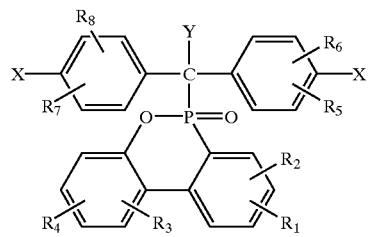

wherein $R_1$–$R_8$ independently are H or $C_1$–$C_4$ alkyl; Y is —OH or

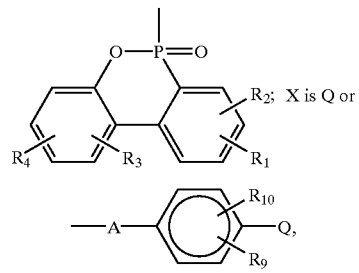

$X$ is Q or wherein Q is H, —$NO_2$, —$NH_2$, —OH, —$CH_3$, —CHO, —COOH,

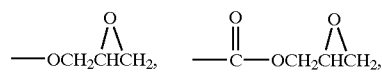

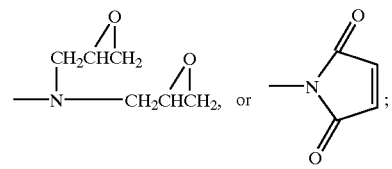

A is —O—,

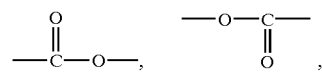

—, —$CH_2$—, or —$C(CH_3)_2$—; $R_9$ and $R_{10}$ independently are H, or $C_1$–$C_4$ alkyl.

12 Claims, 3 Drawing Sheets

COMPOUND A

COMPOUND B

PHOSPHORUS-CONTAINING COMPOUNDS AND THEIR USE IN FLAME RETARDANCE

FIELD OF THE INVENTION

The present invention relates to a series of novel phosphorus-containing compounds and their use as a flame retardant.

BACKGROUND OF THE INVENTION

Besides conventional building materials and textiles, a polymeric material is required to have flame retardance when used in the fabrication of an electronic device, e.g. a printed circuit board, encapsulation resin of an integrated circuit (IC), and electronic connectors, etc. In order to increase the flame retardance of an polymeric material, an addition of a flame retardant is used to achieve this objective regardless of whether the polymer is a thermoset resin or a thermoplastic resin. Organic phosphorus compounds have been widely used as a halogen-free flame retardant to improve or solve the problems such as the formation of toxic fume, corrosion, contamination of dioxin, etc. associated with the use of a halogen-containing flame retardant. Among which, phosphates including aliphatic or aromatic phosphates were widely used in the current products, e.g. triphenylphosphate, tricresylphosphate, and triethylphosphate, etc. These phosphates, after being added into a resin, may cause defects such as insufficient thermal stability and undesired high migration, etc. Therefore, some phosphate oligomers, such as dipolymer of resorcinol diphenyldiphosphate and its oligomer (e.g. Japan Patent 223158, U.S. Pat. No. 5,204,394, and U.S. Pat. No. 5,618,867, etc.), phosphate oligomers having a substituent (e.g. U.S. Pat. No. 5,506,313, EP-A-0456605, and EP-A-0509506, etc.), etc. were developed as a halogen-free flame retardant.

In addition to the requirements of good flame retardance, a polymeric material used in the fabrication of an electronic device also requires excellent electric characteristics, thermal stability, and dimensional stability. The addition of a flame retardant, more or less, will have a certain degree of influence on the properties of the polymeric material. Consequently, it is important for the flame retardant to meet these requirements for this use.

One objective of the present invention is to provide a series of phosphorous-containing compounds with a novel chemical structure.

Another objective of the present invention is to provide a series of novel phosphorous-containing compounds as a flame retardant.

Another objective of the present invention is to provide a flame retardant resinous composition comprising, as a flame retardant, a phosphorous-containing compound of the present invention.

Another objective of the present invention is to provide a cured flame retardant resin which is prepared by cross-linking a flame retardant resinous composition of the present invention.

Still another objective of the present invention is to provide a flame retardant polymer, which is prepared by performing a polymerization reaction of a phosphorous-containing compound of the present invention as a monomer, or a co-polymerization reaction of a phosphorous-containing compound of the present invention as a monomer and another monomer.

SUMMARY OF THE INVENTION

In order to achieve the above-mentioned objectives of the present invention, a phosphorous-containing compound synthesized according to the present invention has the following chemical formula (I):

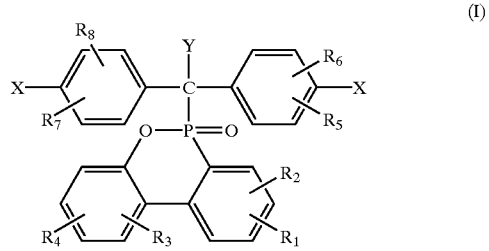

(I)

wherein $R_1$–$R_8$ independently are H or $C_1$–$C_4$ alkyl; Y is —OH or

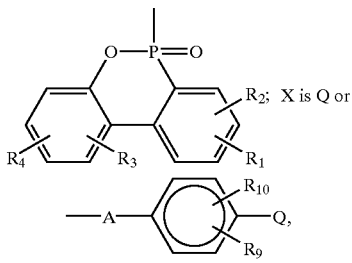

$R_2$; X is Q or wherein $R_1$–$R_4$ are defined as above; Q is H, —$NO_2$, —$NH_2$, —OH, —$CH_3$, —CHO, —COOH,

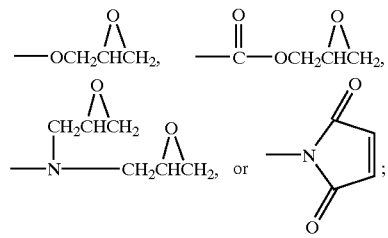

$R_9$ and $R_{10}$ independently are H or $C_1$–$C_4$ alkyl; and A is —O—,

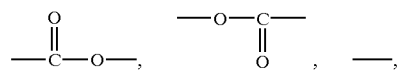

—$CH_2$—, or —$C(CH_3)_2$—.

Preferably, X in the formula (I) is Q.

Preferably, X in the formula (I) is

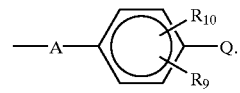

Preferably, $R_1$–$R_8$ in the formula (I) are H, Y is

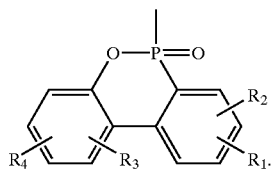

Preferably, Q in the formula (I) is —$NH_2$.
Preferably, Q in the formula (I) is —OH.
Preferably, Q in the formula (I) is

Preferably, A in the formula (I) is —O—.
Preferably, A in the formula (I) is

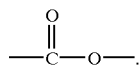

Preferably, A in the formula (I) is

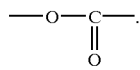

The present invention also provides a flame retardant resinous composition comprising a phosphorous-containing compound having the formula (I).

The present invention also provides a cured flame retardant resin which is prepared by cross-linking the flame retardant resinous composition of the present invention.

The present invention further provides a flame retardant polymer, which is prepared by performing a polymerization reaction of a phosphorous-containing compound having the formula (I) as a monomer, or a co-polymerization of a phosphorous-containing compound having the formula (I) as a monomer and another monomer.

The phosphorous-containing compound (I) of the present invention has the advantages, such as easy to be synthesized, providing a resin of high phosphorous content and high thermal resistance, etc., and thus is suitable to be used as an additive or made into various types of organic polymeric material with flame retardance.

DETAILED DESCRIPTION OF THE INVENTION

The present invention discloses a series of phosphorous-containing compounds having a novel chemical structure and a process for making the same. The new phosphorous-containing compounds of the present invention can be easily synthesized, and can be used to prepare a flame retardant resin having a high phosphorous content and a high thermal stability, so as to improve the defects of a complicated synthesis procedures, a lower phosphorous content, and an insufficient thermal resistance, etc. existing in the conventional phosphorous-containing flame retardant.

In one aspect of the present invention a phosphorous-containing compound synthesized has the following structure:

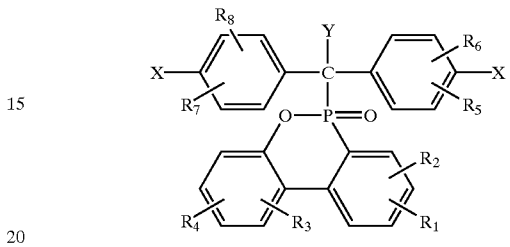

wherein $R_1$–$R_8$ is H, or $C_1$–$C_4$ alkyl, Y is —OH or

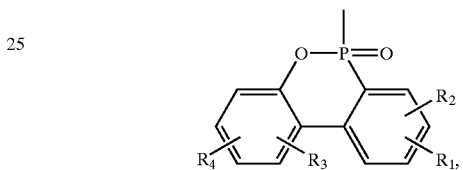

X is —H, —$NO_2$, —$NH_2$, —OH, —$CH_3$, —CHO, —COOH,

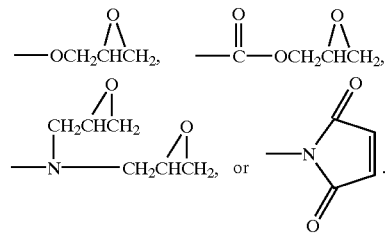

In another aspect of the present invention a phosphorous-containing compound synthesized has the following structure:

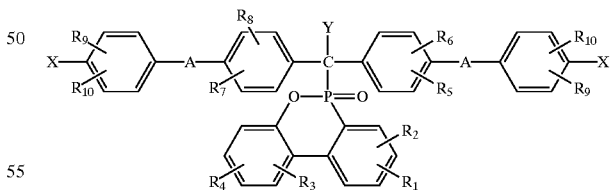

wherein $R_1$–$R_{10}$ is H, or $C_1$–$C_4$ alkyl; Y and X have the same definitions as above; and A is —O—,

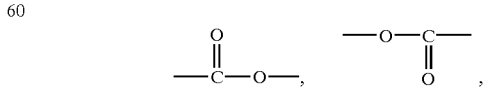

—, —$CH_2$—, —$C(CH_3)_2$—.

A suitable process for synthesizing a phosphorous-containing compound according to the present invention comprises reacting 9,10-dihydro-9-oxa-10-phosphaphenanthrene 10-oxide (abbreviated as DOPO) or DOPO containing -alkyl substituents of the following formula

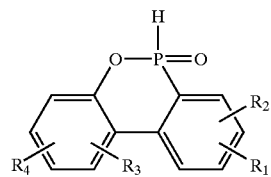

(wherein $R_1$-$R_4$ is H or $C_1$-$C_4$ alkyl) with a compound having —C=O— group at a temperature of 100–200° C., such as a diphenyl ketone derivative. A phosphorous-containing compound having a reactive functional group of the present invention can be synthesized by selecting a diphenyl ketone derivative having a reactive functional group. The phosphorous-containing compounds so synthesized can be used to prepare their derivatives by using the conventional organic synthesis methods.

A phosphorous-containing compound having a reactive functional group of the present invention can undergo a polymerization reaction with another monomer, a grafting reaction or a cross-linking reaction with a polymer to synthesize the corresponding phosphorous-containing flame retardant polymer, or can be added directly into a polymeric material as a flame retardant, which may be used in the fabrication of various electric devices requiring flame retardance.

The present invention can be further understood with the following examples which are used for illustrative purposes and not for limiting the scope of the present invention. The reactions involved in the following examples are shown in the following scheme 1:

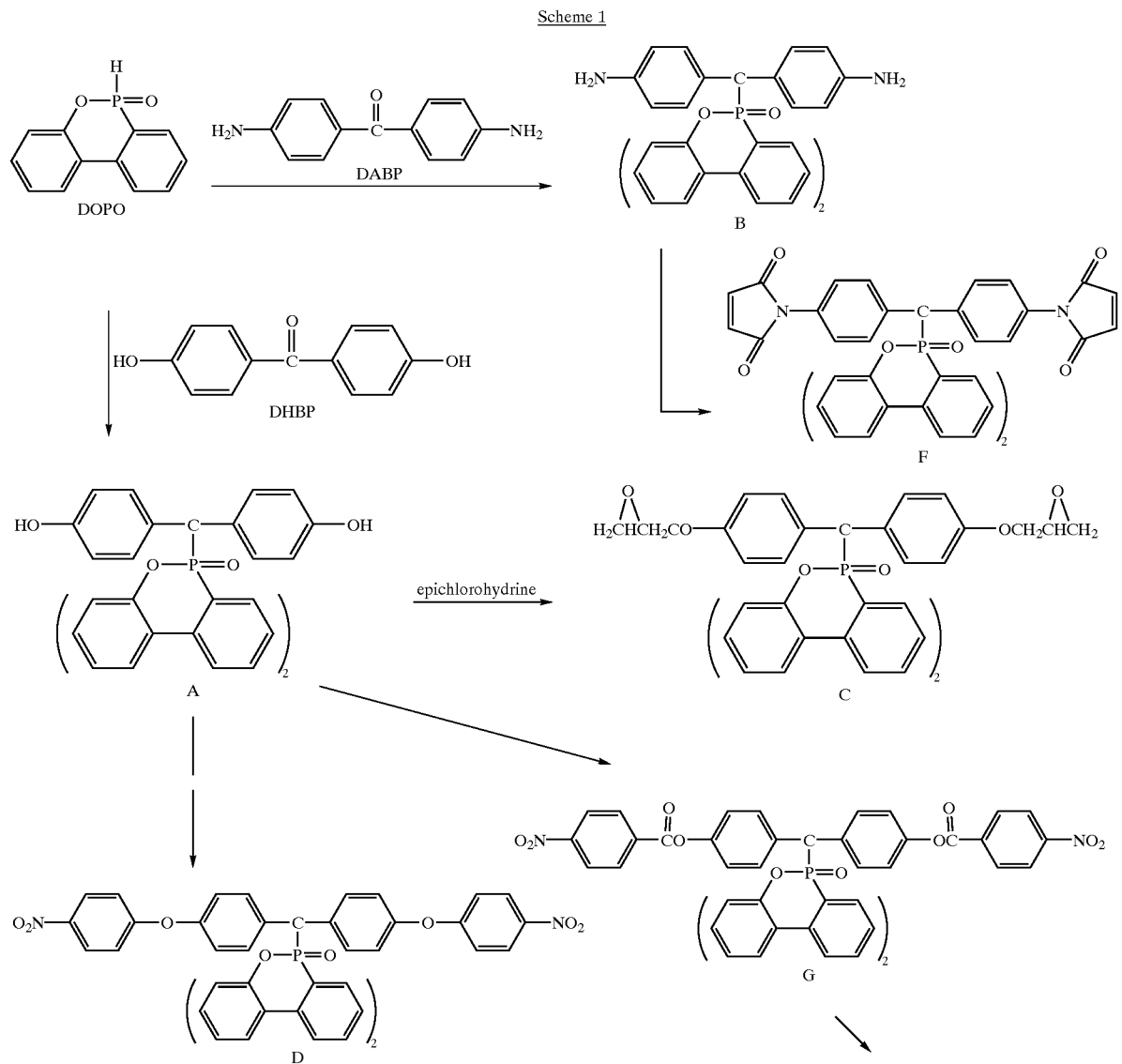

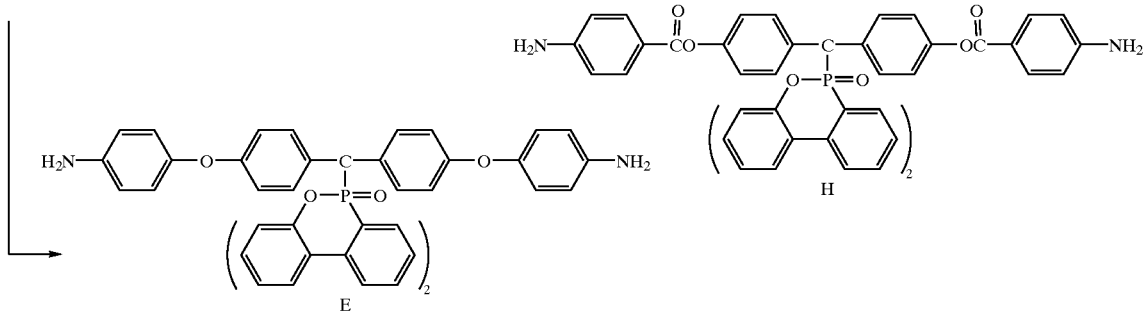

EXAMPLE 1

Synthesis of Compound A

Figure 1:
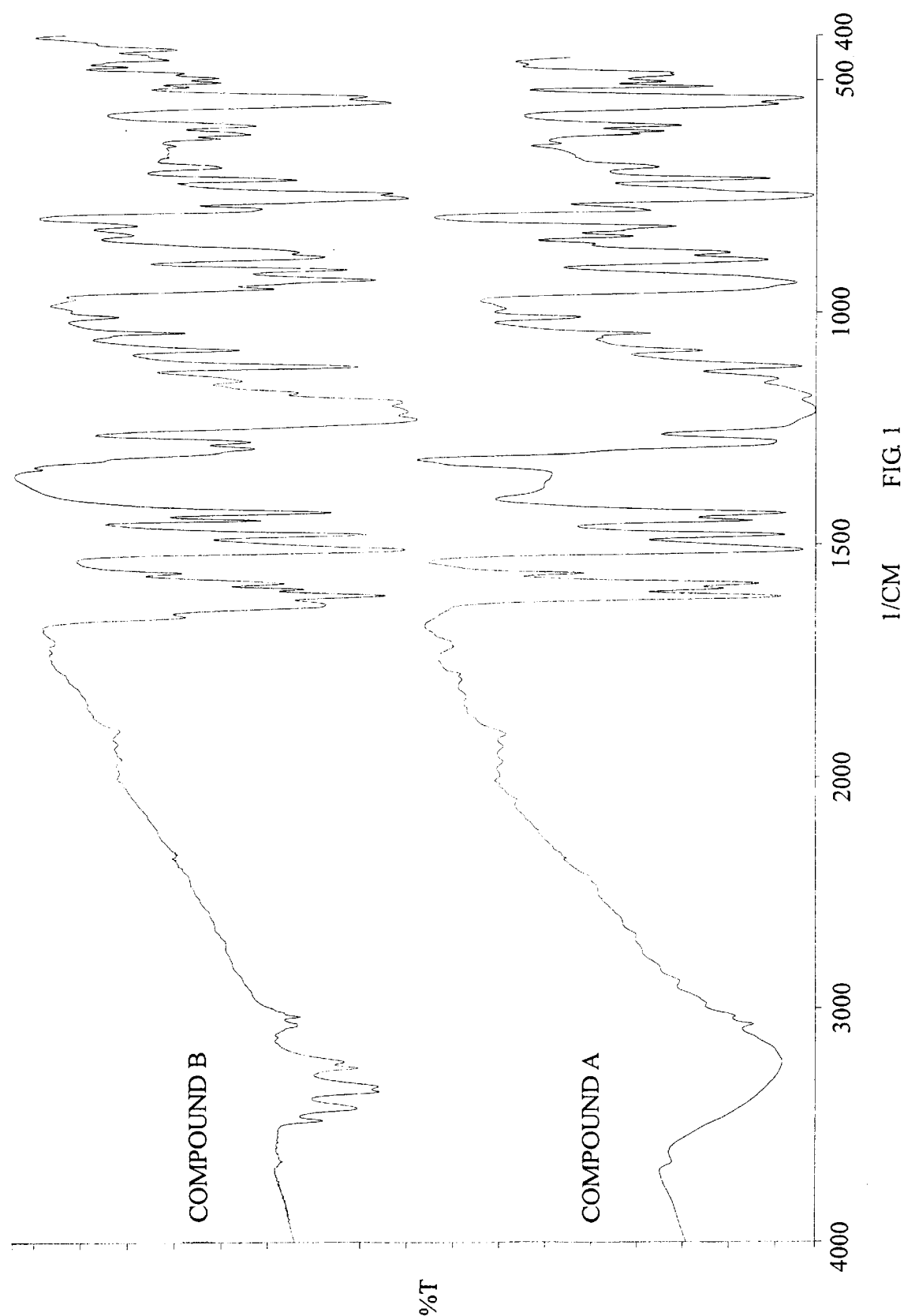
FIG. 1 shows FTIR spectrum of compounds A and B synthesized in Examples 1 and 2 according to the present invention.
Figure 2A:
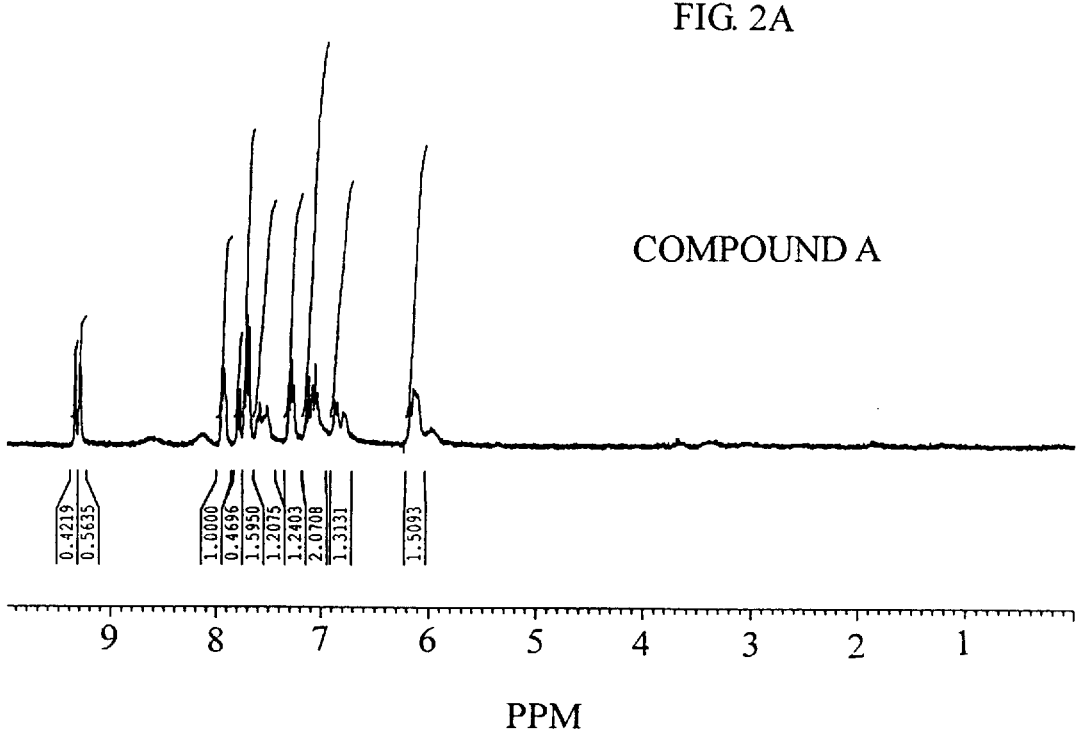
FIGS. 2a and 2b are $^1$H NMR spectrum of compounds A and B synthesized in Examples 1 and 2 according to the present invention, respectively.
Figure 3:
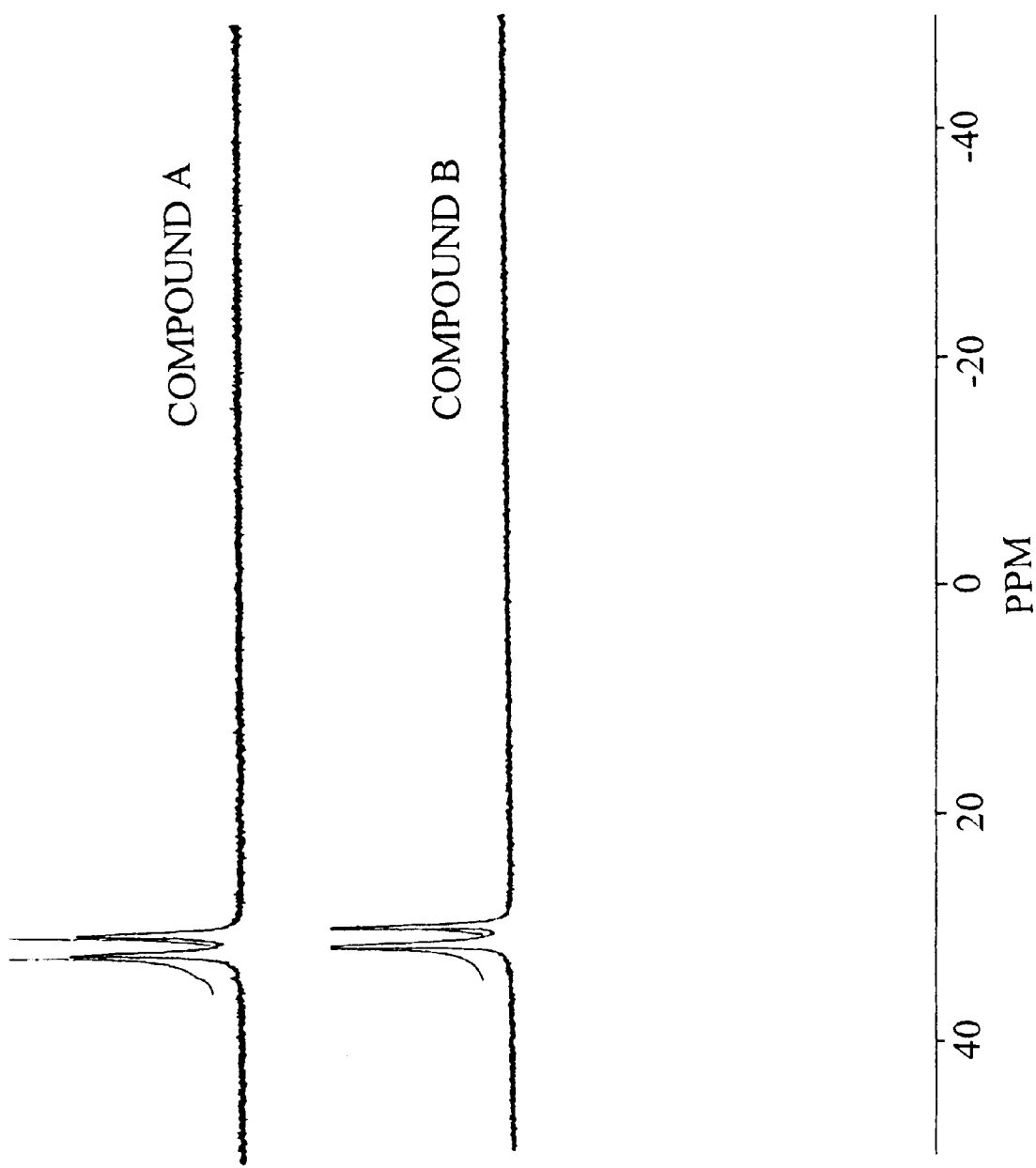
FIG. 3 shows $^{31}$P NMR spectrum of compounds A and B synthesized in Examples 1 and 2 according to the present invention.

To a 1 L three-necked flask equipped with a temperature control and indication device, 512 g of DOPO and 107 g of dihydroxyl-benzophenone were heated to 180° C. The temperature of the reaction system was maintained at 180° C. for three hours, and then 500 ml of toluene was added. After agitation, the mixture was filtered. The resulting solid was washed with 500 ml of tetrahydrofuran twice, filtered and dried in vacuum at 80° C. for two hours to yield a white solid product, a DOPO derivative compound A having two hydroxyl groups. The FTIR spectrum, the $^1$H NMR spectrum and the $^{31}$P NMR spectrum of the compound A are shown in FIG. 1, FIG. 2a and FIG. 3, respectively.

EXAMPLE 2

Synthesis of Compound B

Figure 2B:
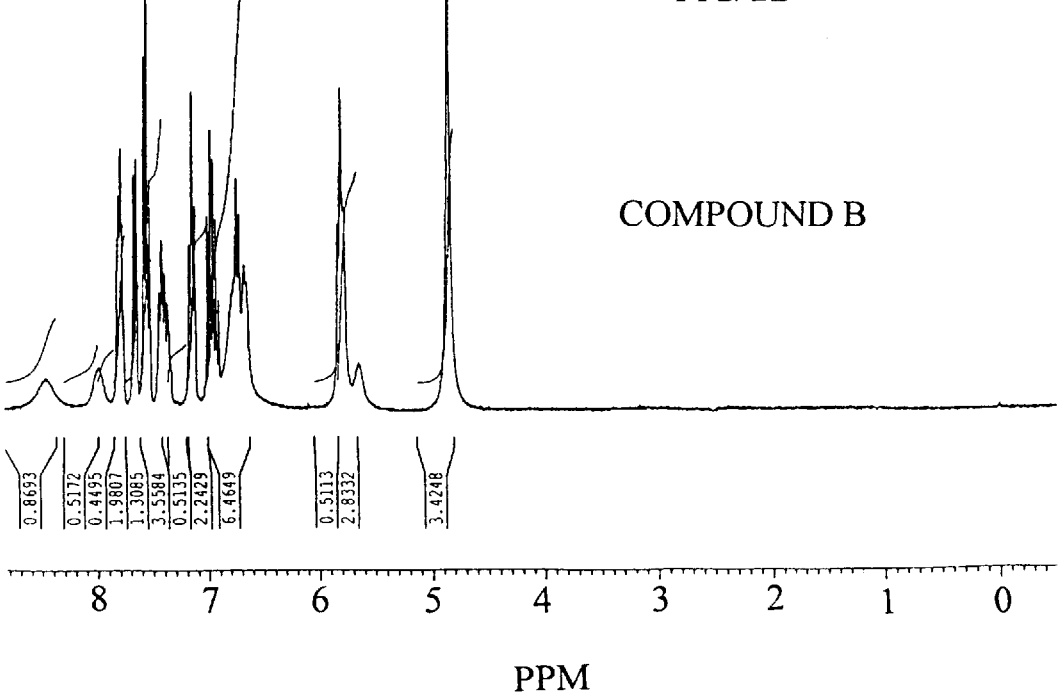

The steps in Example 1 were repeated except that diamino-benzophenone was used to replace dihydroxyl-benzophenone. A white solid product having two amino groups, a DOPO derivative compound B, was obtained. The FTIR spectrum, the $^1$H NMR spectrum, and the $^{31}$P NMR spectrum are shown in FIG. 1, FIG. 2b and FIG. 3, respectively.

EXAMPLE 3

Synthesis of Compound C

To a 3 L four-necked flask equipped with a temperature and pressure control and indication device, 300 g of a DOPO derivative compound A having two hydroxyl groups and 1000 g of epichlorohydride were added. The flask was also equipped with a device capable of condensing and separating an azeotropic mixture of water and epichlorohydride into an oil phase and an aqueous phase. This mixture was agitated to become a homogeneous solution under atmospheric pressure, and was then heated to 70° C. under an absolute pressure of 190 mmHg. At an equilibrium temperature and pressure of this solution, 80.2 g of 49.3% sodium hydroxide solution was added to the solution with a constant rate within four hours. While the sodium hydroxide solution was being added, water in the reaction system was removed by an azeotropic distillation. The azeotrope, after condensation, was separated into an oil phase and an aqueous phase. The oil phase was continuously recycled to the reaction system, and the aqueous phase was removed. After completion of the reaction, the unreacted epichlorohydride and solvent were removed by distillation under a reduced pressure. The crude epoxy resin thus formed was dissolved by methyl ethyl ketone, mixed with deionized water to wash away sodium chloride in the resin. The dissolved epoxy solution was subsequently distilled under a reduced pressure to remove the methyl ethyl ketone thereby obtaining a pale yellow epoxy-containing DOPO derivative C with an epoxy equivalent of 378.

EXAMPLE 4

Synthesis of Compound D

To 600 ml of dimethylformamide (DMF) in an one-liter three-necked flask reactor equipped with a temperature control and indication device, 100 g of DOPO derivative A having two hydroxyl groups, 50 g of p-chloro nitro-benzene and 44 g of potassium carbonate were added and dissolved. The solution was heated and reacted under refluxing for 8 hours, and then the temperature of the solution was cooled to room temperature. A mixture of methanol and water (1:1) was added to the reaction mixture to form a precipitate. A solid product D was yielded after the precipitate was washed with toluene and tetrahydrofuran, and dried in vacuum at 80° C. for 3 hours.

EXAMPLE 5

Synthesis of Compound E

To an one-liter three-necked flask reactor equipped with a temperature control and indication device, 80 g of compound D, 110 g of stannous chloride, 500 ml of ethanol and 150 ml of concentrated hydrochloric acid were added and stirred at room temperature for four hours. The reaction solution was concentrated by a rotary evaporation device. The precipitate was filtered, neutralized with 25% sodium hydroxide aqueous solution, and recrystallized with ethanol to yield a solid product E.

EXAMPLE 6

Synthesis of Compound F

In an one-liter three-necked reactor equipped with a temperature control and indication device, 30 g of maleic anhydride was dissolved in 200 ml of acetone. The flask was placed in an ice bath. 60 g of compound B (synthesized in Example 2) in 400 ml of acetone was added into the flask. After four hours of reaction, 50 ml of acetic acid anhydride and 8.5 g of sodium acetate were added. The mixture was reacted at 60° C. for four hours. The resulting reaction mixture was concentrated by a rotary evaporation device, and ethanol was added thereto form a precipitate. After filtration, the precipitate was recrystallized with ethanol to yield a solid product F.

EXAMPLE 7

Synthesis of Compound G

To 62 g of compound A (synthesized in Example 1) in 400 ml of DMF in an one-liter three-necked flask container equipped with a temperature control and indication device under dry nitrogen atmosphere, 23 g of tri-ethyl amine was added. The flask was placed in an ice bath. 41 g of nitro-benzoyl chloride was slowly added to the solution in ice bath within one hour. Upon completion of the addition, the reaction was continued at room temperature for four hours. The reaction mixture was filtered and the resulting precipitate was recrystallized with DMF to obtain a solid product G.

EXAMPLE 8

Synthesis of Compound H

The procedures of Example 5 were repeated to obtain a solid product H, except that the compound D was replaced by the compound G from Example 7.

What is claimed is:

1. A phosphorous-containing compound having the following chemical formula (I):

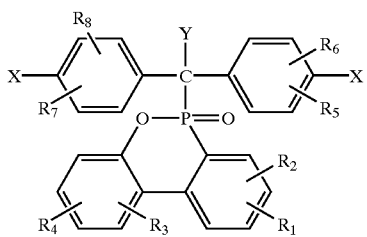

(I)

wherein $R_1$–$R_8$ independently are H or $C_1$–$C_4$ alkyl; Y is —OH or

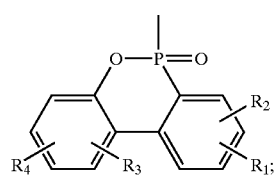

X is Q or

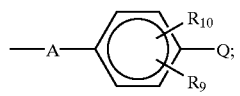

wherein $R_1$–$R_4$ are defined as above; Q is H, —$NO_2$, —$NH_2$, —OH, —$CH_3$, —CHO, —COOH,

-continued

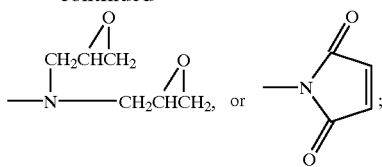

$R_9$ and $R_{10}$ independently are H or $C_1$–$C_4$ alkyl; and A is —O—,

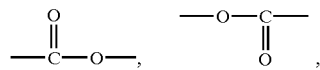

—, —$CH_2$—, or —$C(CH_3)_2$—.

2. The compound as claimed in claim 1, wherein X in the formula (I) is Q.

3. The compound as claimed in claim 1, wherein X in the formula (I) is

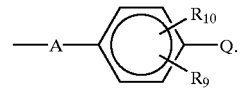

4. The compound as claimed in claim 3, wherein A is —O—.

5. The compound as claimed in claim 3, wherein A is

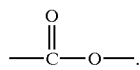

6. The compound as claimed in claim 3, wherein A is

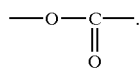

7. The compound as claimed in claim 1, wherein $R_1$–$R_8$ in the formula (I) are H, and Y is

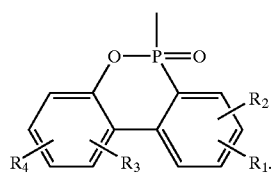

8. The compound as claimed in claim 1, wherein Q in the formula (I) is —$NH_2$.

9. The compound as claimed in claim 1, wherein Q in the formula (I) is —OH.

10. The compound as claimed in claim 1, wherein Q in the formula (i) is

11. A flame retardant resinous composition comprising a phosphorous-containing compound (I) as defined in claim 1 as a flame retardant.

12. A cured flame retardant resin prepared by cross-linking the flame retardant resinous composition of claim 11.

* * * * *